US011152091B1

United States Patent
Makarskyy et al.

(10) Patent No.: US 11,152,091 B1
(45) Date of Patent: Oct. 19, 2021

(54) SYSTEMS AND METHODS FOR CLINICAL TASK SEPARATION IN ELECTRONIC HEALTH RECORD APPLICATIONS

(71) Applicant: Allscripts Software, LLC, Raleigh, NC (US)

(72) Inventors: Stanislav Makarskyy, Arlington Heights, IL (US); Ethan O'Brien, Raleigh, NC (US); Mark Gregory Plunkett, Libertyville, IL (US); Ankit Singh, Apex, NC (US); Igor Chmil, Buffalo Grove, IL (US)

(73) Assignee: ALLSCRIPTS SOFTWARE, LLC, Raleigh, NC (US)

( * ) Notice: Subject to any disclaimer, the term of this patent is extended or adjusted under 35 U.S.C. 154(b) by 0 days.

(21) Appl. No.: 16/779,093

(22) Filed: Jan. 31, 2020

(51) Int. Cl.
  *G06F 3/048* (2013.01)
  *G16H 20/10* (2018.01)
  *G06F 3/0482* (2013.01)
  *G06F 3/0484* (2013.01)
  *G16H 10/60* (2018.01)

(52) U.S. Cl.
  CPC ........... *G16H 20/10* (2018.01); *G06F 3/0482* (2013.01); *G06F 3/0484* (2013.01); *G16H 10/60* (2018.01)

(58) Field of Classification Search
  CPC ...... G16H 20/10; G16H 10/60; G06F 3/0482; G06F 3/0484
  See application file for complete search history.

(56) References Cited

U.S. PATENT DOCUMENTS

| | | |
|---|---|---|
| 2012/0215560 A1 | 8/2012 | Ofek et al. |
| 2018/0181712 A1 | 6/2018 | Ensey et al. |
| 2018/0181716 A1 | 6/2018 | Mander et al. |

FOREIGN PATENT DOCUMENTS

WO  2008144676 A2  11/2008

*Primary Examiner* — Pei Yong Weng
(74) *Attorney, Agent, or Firm* — Medley, Behrens & Lewis, LLC

(57) ABSTRACT

A server EHR executing on a server computing device is in communication with a client EHR executing on a first client computing device, and receives a prescription authorization from the client EHR, the prescription authorization based on input received from an authorized clinician user of the client EHR during performance of a clinical subtask of a prescription ordering task. The server EHR assigns a non-clinical subtask of the prescription ordering task to a non-clinician user operating a client application executing on a second client computing device. The non-clinician user provides input to the client application that pertains to completion of the non-clinical subtask. The client application transmits prescription ordering data to the server EHR, whereupon the server EHR outputs a prescription order to a second server computing device associated with a pharmacy indicated in the prescription ordering data.

20 Claims, 6 Drawing Sheets

SYSTEMS AND METHODS FOR CLINICAL TASK SEPARATION IN ELECTRONIC HEALTH RECORD APPLICATIONS

BACKGROUND

Electronic health record applications (EHRs) are now commonly used in connection with performing various clinical and non-clinical tasks in healthcare environments. For example, and not by way of limitation, EHRs facilitate various tasks performed by healthcare workers related to patient intake, billing, insurance, updating medical records, prescribing medication, tracking care over time, and so forth.

EHRs are commonly configured to assist clinicians and other healthcare workers in connection with these various tasks by way of graphical user interfaces (GUIs) that prompt users for input of specific types relating to a predefined task. In a non-limiting example, in connection with a clinician collecting patient data during a first appointment with a patient, a conventional EHR can present the clinician with a GUI that includes fields for entry of information relating to the patient (e.g., demographic information, symptoms, presenting complaint, etc.). By way of another example, a conventional EHR can present a GUI to a non-clinician user of the EHR, such as a clerical or other administrative worker, where the GUI includes fields for display and entry of information relating to billing or insurance information with respect to care of a patient provided by a healthcare enterprise. Accordingly, conventionally EHRs are configured to present interfaces to clinicians that are configured to assist clinicians in the performance of clinical tasks, and are configured to present interfaces to non-clinician healthcare workers that are configured to assist such non-clinician healthcare workers with non-clinical tasks.

In some cases, however, a clinical task such as ordering a prescription for a patient can include both clinical and non-clinical subtasks. For example, ordering a prescription involves clinical functions such as diagnosing a condition or illness of a patient and selecting a suitable medication and dosage, and non-clinical functions such as selecting a pharmacy from which the prescription is to be fulfilled Conventionally, EHRs are configured to ensure that clinical tasks are performed only by authorized clinician users of the EHR. Accordingly, conventional EHRs generally require an authorized clinician user to be logged in to the EHR to perform all aspects of a clinical task from start to finish. Therefore, a conventional EHR requires an authorized clinician user to be logged in to a client EHR when a task includes both clinical and non-clinical subtasks. This requires either that a clinician using a conventional EHR performs non-clinical subtasks for which the clinician's expertise is not required, or that a non-clinician performs the non-clinical subtasks using the clinician's credentials, creating risks to EHR security, documentation integrity, legal liability, and potentially the health of patients.

SUMMARY

The following is a brief summary of subject matter that is described in greater detail herein. This summary is not intended to be limiting as to the scope of the claims.

Various technologies are described herein that pertain to an EHR system that assigns clinical subtasks of a clinical task to a clinician user of the EHR and that assigns non-clinical subtasks of a clinical task to a non-clinician user of the EHR. Stated differently, an EHR system is described herein that facilitates separation of mixed clinical and non-clinical tasks into clinical and non-clinical components that are separately assigned to clinician and non-clinician users of the EHR, respectively.

An exemplary computing system includes a server computing device that executes a server EHR and a first client computing device that executes a client EHR that is configured to communicate with the server EHR. The exemplary computing system further includes a second client computing device that executes a second client application. A clinician user registered with the server EHR is logged into the first client computing device. A non-clinician user operates the second client computing device. The non-clinician user is registered with the server EHR or a different application that is configured to communicate with the server EHR (e.g., a patient portal application).

In a non-limiting example, a clinician user of the client EHR initiates a prescription ordering task by way of the client EHR. The prescription ordering task can be indicated in task data stored at the server computing device as including both a clinical subtask and a non-clinical subtask. The client EHR displays, on a display of the first client computing device, a first GUI that pertains to the clinical subtask of the prescription ordering task. For example, the first GUI can include one or more fields configured to receive input by way of which the clinician user of the first client computing device can select a medication and dosage of the selected medication to be prescribed to a patient. The client EHR can be configured to output prescription authorization data to the server EHR responsive to completion of the clinical subtask of the prescription ordering task. By way of example, responsive to the clinician user of the client EHR setting forth a selection of a medication to be prescribed to the patient, the client EHR can output a prescription authorization to the server EHR that indicates that the clinician has authorized the selected medication to be prescribed to the patient.

Responsive to the clinical subtask being completed (e.g., responsive to receipt of the prescription authorization from the client EHR), the server EHR assigns a non-clinical subtask of the prescription ordering task to the non-clinician user of the second client computing device. Thereafter, the clinician user can perform other, unrelated tasks by way of the client EHR prior to completion of the non-clinical subtasks. In exemplary embodiments, the non-clinician user can be registered with the server EHR, whereupon the server EHR assigns the task to the non-clinician user in task data maintained by the server EHR. In other embodiments, the non-clinician user is not registered with the server EHR directly but is registered to a patient portal application with which the server EHR is configured to operate. In such embodiments, the server EHR outputs task data to a server patient portal application executing on a second computing device, whereupon the server patient portal application assigns the task to the non-clinician user who is registered with the patient portal application.

Based upon the non-clinical subtask being assigned to the non-clinician user of the second client computing device, the second client application is caused to display a second GUI on a display of the second client computing device, wherein the second GUI pertains to the non-clinical subtask. The non-clinician user of the second client computing device can complete the non-clinical subtask by providing input to the second client application by way of the second GUI. Continuing the example set forth above, the non-clinician user of the second client computing device can select a pharmacy from which the prescription authorized by the clinician user is to be filled.

Responsive to the non-clinical subtask being completed, the second client application can output prescription ordering data to the server EHR (e.g., by transmitting the data directly to the server EHR or by submitting the data to a patient portal server application that subsequently transmits the prescription ordering data to the server EHR). Upon receipt of the prescription ordering data, the server EHR can transmit a prescription order to a third computing device that is maintained by a pharmacy (e.g., the pharmacy selected by the non-clinician user of the second client computing device). In exemplary embodiments, the prescription order comprises data indicating that the clinician user has authorized dispensing of the medication to the patient.

Embodiments set forth herein present several advantages over conventional EHR systems in connection with prescription ordering. Clinician users of an EHR can save time by not being required by the EHR to complete non-clinical aspects of a prescription ordering process such as selecting a pharmacy to which to submit a prescription order or selecting brand name versus generic medications. Security of credentialed accounts is improved since credentials need not be shared in order to allow clinical and non-clinical subtasks to be performed by different people on different computing devices. Further, embodiments described herein allow clinical and non-clinical subtasks of a prescription ordering task to be performed at different times and places. For instance, a clinical subtask of the prescription ordering task can be performed while a patient is in a face-to-face appointment with a clinician, whereas a non-clinical subtask of the prescription ordering task can be performed by another person (e.g., a non-clinical healthcare worker or the patient) at a later date or a different place.

The above summary presents a simplified summary in order to provide a basic understanding of some aspects of the systems and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the more detailed description that is presented later.

DETAILED DESCRIPTION

Figure 1:
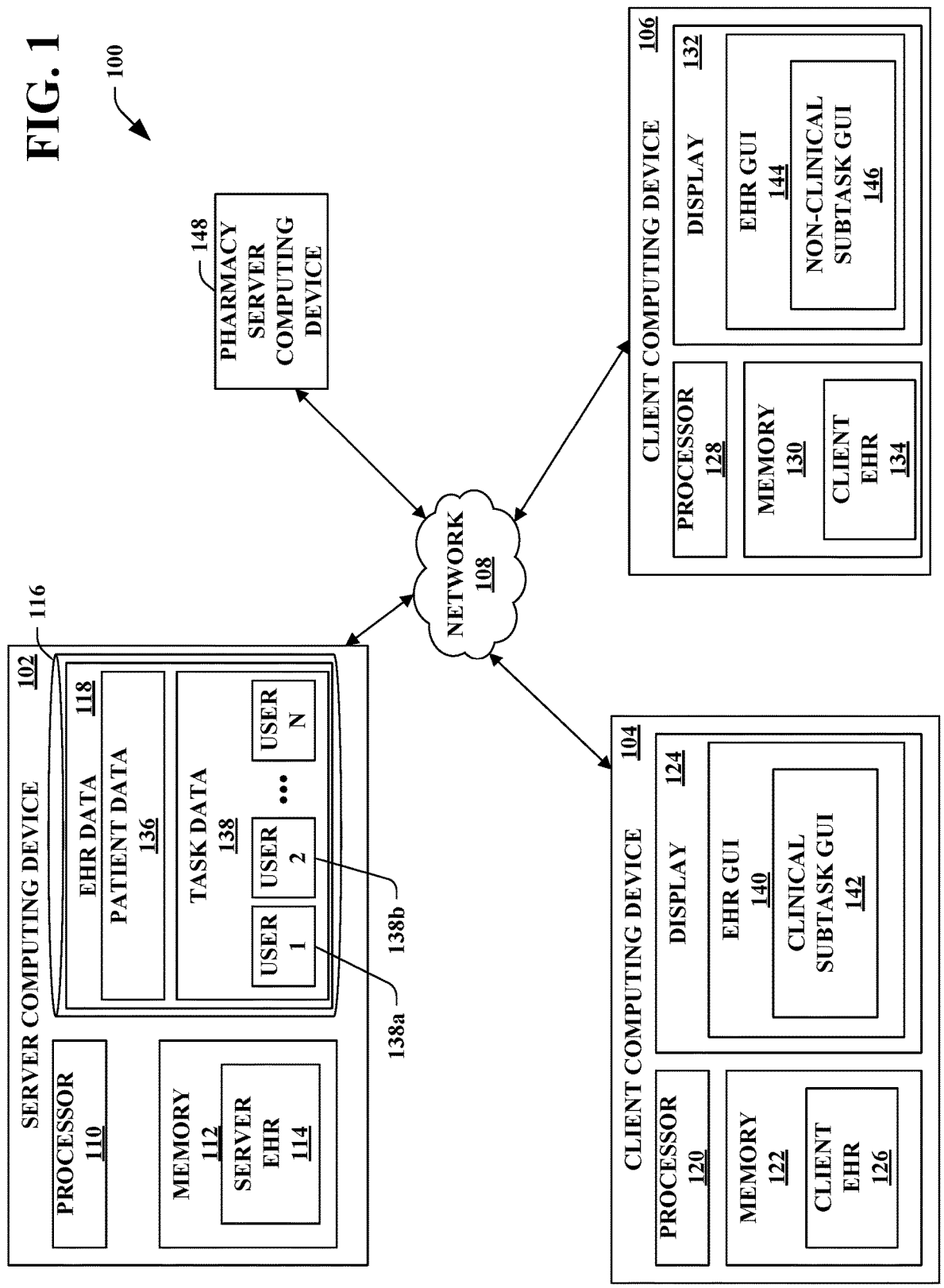
FIG. 1 is a functional block diagram of an exemplary EHR system that facilitates assignment of clinical subtasks to clinician users and non-clinical subtasks to non-clinician users.

Various technologies pertaining to an EHR that facilitates separately assigning clinical subtasks of a clinical task to a clinician user of the EHR and non-clinical subtasks of the clinical task to a non-clinician user of the EHR are now described with reference to the drawings, wherein like reference numerals are used to refer to like elements throughout. In the following description, for purposes of explanation, numerous specific details are set forth in order to provide a thorough understanding of one or more aspects. It may be evident, however, that such aspect(s) may be practiced without these specific details. In other instances, well-known structures and devices are shown in block diagram form in order to facilitate describing one or more aspects. Further, it is to be understood that functionality that is described as being carried out by certain system components may be performed by multiple components. Similarly, for instance, a component may be configured to perform functionality that is described as being carried out by multiple components.

Moreover, the term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form.

Further, as used herein, the terms "component" and "system" are intended to encompass computer-readable data storage that is configured with computer-executable instructions that cause certain functionality to be performed when executed by a processor. The computer-executable instructions may include a routine, a function, or the like. It is also to be understood that a component or system may be localized on a single device or distributed across several devices. Further, as used herein, the term "exemplary" is intended to mean serving as an illustration or example of something, and is not intended to indicate a preference.

Generally, an EHR is a distributed application that includes a client EHR executing on a client computing device and a server EHR executing on a server computing device. The client EHR, briefly, is configured to display data to a healthcare worker and receive input from the healthcare worker, while the server EHR is configured to acquire data based upon information received from the client EHR and transmit information to the client EHR for presentment by way of the client EHR.

Similarly, a patient portal application is a distributed application that includes a patient portal client executing on a client computing device and a patient portal server executing on a server computing device. The patient portal client is configured to display data to a patient and/or healthcare worker and to receive input from the patient and/or healthcare worker. The patient portal server is configured to acquire data based upon information received from the patient portal client and optionally other applications such as EHRs, health information exchanges (HIEs), etc., and to transmit information to the patient portal client for presentment by way of the patient portal client.

With reference to FIG. 1, an exemplary computing system 100 that facilitates assignment of clinical subtasks to clinician users of an EHR and non-clinical subtasks to non-clinician users is illustrated. The system 100 includes a server computing device 102, a first client computing device 104, and a second client computing device 106. Each of the first client computing device 104 and the second client computing device 106 is in communication with the server computing device 102 by way of a network 108. The network 108 can be or include a local area network (LAN), such as a local network maintained by a healthcare facility, a wide area network (WAN), such as the Internet, or other suitable means of network communication. It is further to be understood that while a single network is shown, the network 108 can be embodied by multiple inter-connected networks. By way of example, and not limitation, the client computing devices 104, 106 can be connected to a same local area network, and the server computing device 102 can be connected to each of the client computing devices 104, 106 by way of the Internet. In such embodiments, the server computing device 102 can be a cloud computing device that is located remotely from either of the client computing devices 104, 106. The client computing devices 104, 106 can be embodied as any of various types of computing device such as desktop computing devices, laptop computing devices, kiosks, or mobile computing devices such as tablets and smartphones.

The server computing device comprises a processor 110, memory 112 that stores instructions that are executed by the processor 110. The memory 112 has a server EHR 114 loaded therein. The server computing device 102 further comprises a datastore 116 that stores various EHR data 118 that are accessed by the server EHR 114 in connection with performing functions in support of various tasks of a healthcare enterprise (e.g., a healthcare enterprise that maintains or controls the server computing device 102).

The first client computing device 104 comprises a processor 120, memory 122 that stores instructions that are executed by the processor 120, and a display 124. The memory 122 has a first client EHR 126 loaded therein. The second client computing device 106 comprises a processor 128, memory 130 that stores instructions that are executed by the processor 128, and a display 132. The memory 130 has a second client EHR 134 loaded therein.

The server EHR 114 of the server computing device 102 maintains the EHR data 118 in connection with receiving data from and outputting data to the first client EHR 126 and the second client EHR 134 as the client EHRs 126, 134 are used to facilitate various tasks related to providing healthcare services. By way of example, the EHR data 118 includes patient data 136 such as demographic information pertaining to patients, information relating to presenting complaints, symptoms, and diagnoses of patients, insurance information, and other information relating to patients that may be pertinent to provision of care to a patient by a healthcare enterprise. In exemplary embodiments, the patient data 136 can be or include a plurality of electronic medical records, wherein each medical record comprises information pertaining to a particular patient. The EHR data 118 further includes task data 138 for each of a plurality of N users registered with the server EHR 114, where N is a positive integer. The task data 138 indicates, for each of the registered users, tasks that are assigned to the user. For example, the task data 138 can include first task data 138a that includes tasks assigned to a first user (e.g., a clinician user), and can further include second task data 138b that includes tasks assigned to a second user (e.g., a non-clinician user). In non-limiting examples, a task assigned to a clinician user can indicate that the clinician is to perform a test with respect to a patient, or that the clinician is to conduct a follow-up appointment with the patient. In other non-limiting examples, a task assigned to a non-clinician user can indicate that the non-clinician user is to process billing or insurance paperwork pertaining to a patient encounter, or that the non-clinician user is to schedule a follow-up appointment between a patient and a clinician.

The first client computing device 104 is operated by a clinician user who is registered with the server EHR 114. In connection with using the first client EHR 126, the clinician user sets forth user credentials that are authorized by the server EHR 114 to enable access to the first client EHR 126 by the clinician user. Thus, the client EHR 126 associates a computing session and actions taken during that computing session with the clinician user of the first client computing device 104. Responsive to receiving an indication of authorization of the user credentials (e.g., from the server EHR 114 in response to the client EHR 126 providing the user credentials to the server EHR 114), the first client EHR 126 displays an EHR GUI 140 that may be customized in various respects for the clinician user. For instance, the EHR GUI 140 can include identifiers of patients who are being treated by the clinician user, indications of tasks assigned to the clinician user (e.g., in the task data 138a), messages addressed to the clinician user, etc.

By interacting with the EHR GUI 140, the clinician user of the first client computing device 104 can initiate performance of a task by way of the client EHR 126. By way of example, the clinician user can interact with the EHR GUI 140 to initiate a first-time patient visit task, a follow-up consultation task, a prescription ordering task, etc. In various embodiments, a task initiated by the clinician user of the first client computing device 104 can be a task that is included in the task data 138a that is assigned to the clinician user. In such embodiments, for example, the client EHR 126 can display, in the EHR GUI 140, an indication of one or more tasks that are currently assigned to the clinician user. The clinician user can select a currently assigned task by way of the EHR GUI 140. Responsive to the selection, the server EHR 114 returns a portion of the task data 138a to the client EHR 126, whereupon data and/or an interface pertaining to performance of the task is displayed by the client EHR 126 in the EHR GUI 140. The client EHR 126 can be configured to display different data in the EHR GUI 140 for each of a plurality of different tasks that can be performed by the clinician user by way of the client EHR 126. In further embodiments, the clinician user can initiate, by way of the client EHR 126, a task that is not already assigned to the clinician user in the task data 138a. In response to receipt of user input indicating initiation of the task, the client EHR 126 outputs an indication that the task has been initiated to the server EHR 114. Responsive to receiving the indication, the server EHR 114 creates task data pertaining to the task and indicating that the clinician is performing or is assigned to perform the task. The server EHR 114 can store the created task data as part of the task data 138a that is assigned to the clinician user.

Similarly, a non-clinician user of the client EHR 134 that executes on the client computing device 106 can initiate, by way of the client EHR 134, performance of a task that is included in the task data 138b that is assigned to the non-clinician user of the client EHR 134. The non-clinician user of the client EHR 124 can also initiate a task by way of the client EHR 134, responsive to which the server EHR 114 creates task data for the task that is included in the task data 138*b* assigned to the non-clinician user.

In various embodiments, a task to be performed by a user of either of the client computing devices 104, 106 can include both clinical subtasks and non-clinical subtasks. Generally, clinical subtasks are tasks that are required by law, policy, or other regulation to be performed by authorized clinicians. By way of example, and not limitation, a clinical subtask can be or include diagnosing a patient condition based on symptoms of the patient, prescribing a medication to treat a patient condition, ordering a diagnostic test to be performed with respect to a patient, etc. Non-clinical subtasks are tasks that are permitted to be performed by non-clinician healthcare workers. Non-clinical subtasks can include, for example, billing- and insurance-related tasks, scheduling tasks (e.g., scheduling an appointment with a clinician for a patient), data entry, and the like.

Conventionally, EHRs are configured such that a prescription ordering task is performed by a single clinician user of the EHR. Accordingly, a conventional EHR requires a client EHR that is logged in with a clinician user's credentials to perform all aspects of the prescription ordering task, even if only non-clinical subtasks of the prescription ordering task remain uncompleted. Thus, a conventional EHR requires some of a prescription ordering task to be performed by a clinician user of the EHR even though a non-clinician user may be able and authorized to perform the non-clinical subtasks.

The computing system 100 allows multiple users to jointly perform one or more tasks by way of the client EHRs 126, 134, such that a first user (e.g., a clinician user) interacting with a first computing device performs clinical subtasks of a mixed clinical/non-clinical task and a second user (e.g., a non-clinician user) interacting with a second computing device performs non-clinical subtasks of the mixed task. This can save computing resources such as compute time by allowing a non-clinical subtask to be performed at a computing device other than the computing device that initiated the prescription ordering task.

Various exemplary operations of the computing system 100 are now described. A clinician user of the client computing device 104 can initiate the prescription ordering task during a consultation or other visit with a patient. Responsive to the clinician user initiating the prescription ordering task (e.g., by selection of a selectable element of the EHR GUI 140 that corresponds to the prescription ordering task), the client EHR 126 causes a clinical subtask GUI 142 to be displayed within the EHR GUI 140. The clinical subtask GUI 142 prompts the clinician for input relating to performance of a clinical subtask of the prescription ordering task. In an exemplary embodiment, the clinical subtask GUI 142 can include a field for selection of a medication that is to be prescribed to a patient. By way of example, and not limitation, the field can be or include a list of medications from which a medication that is to be prescribed to a patient can be selected. In further non-limiting examples, the field can be or include a search field. The clinical subtask GUI 142 can further include a means for the clinician user to provide input indicating that the clinician user has authorized a prescription for the selected medication for the patient. In non-limiting examples, the clinical subtask GUI 142 can include a prescription authorization button, a touch- or gesture-sensitive input region for receipt of a signature of the clinician, or other means by way of which the clinician can indicate her authorization for the medication to be dispensed to the patient.

When the clinical subtask has been completed (e.g., by receipt of a selection of a medication and an indication of authorization by way of the clinical subtask GUI 142), the first client EHR 126 outputs a prescription authorization to the server EHR 114. The prescription authorization can indicate the medication selected by the clinician user of the first client computing device 104 and that the medication is authorized by the clinician user to be dispensed to the patient. Once the prescription authorization has been output to the server EHR 114, the first client EHR 126 is configured to permit the clinician user of the first client computing device 104 to perform other tasks unrelated to the prescription ordering task. Whereas a conventional EHR would require the clinician user to perform additional non-clinical tasks to complete the prescription ordering task (e.g., selecting a pharmacy to which to send the prescription authorization), the first client EHR 126 allows the clinician user to perform other tasks that are unrelated to the prescription ordering task once the clinical subtask has been completed.

Responsive to receipt of the prescription authorization, the server EHR 114 assigns a non-clinical subtask to a second non-clinician user in the plurality of N users registered with the server EHR 114 upon receiving the prescription authorization from the first client EHR 126. For example, the server EHR 114 can update a portion of the task data 138 associated with the second non-clinician user to indicate that the non-clinical subtask is assigned to the second non-clinician user. The server EHR 114 can assign the non-clinical subtask to a non-clinician user based upon input received at the first client EHR 126. In a non-limiting example, the clinical subtask GUI 142 of the first client EHR 126 can include a field for selection of a non-clinician user from amongst a plurality of non-clinician users. The clinical subtask GUI 142 can include a list of users that are registered with the server EHR 114 and that are authorized to perform non-clinical subtasks with respect to a prescription order. The clinician user of the client EHR 126 can select a non-clinician user to which the clinician user would like the non-clinical subtask assigned. The prescription authorization output by the client EHR 126 to the server EHR 114 can include data indicative of the selected non-clinician user. The server EHR 114 can then assign the non-clinical subtask to the non-clinician user based upon the prescription authorization indicating the non-clinician user.

In various embodiments, the server EHR 114 can update the task data 138 such that the non-clinical subtask expires and is no longer available for completion to the second non-clinician user when a proscribed amount of time has passed. The expiration time of the non-clinical subtask can be a default expiration time assigned by the server EHR 114, or can be an expiration time selected by the clinician user of the client EHR 126 during completion of the clinical subtask of the prescription ordering task. Accordingly, the clinician user can authorize a prescription to be filled within a specified time period, after which the authorization is no longer valid.

Subsequently, the second non-clinician user logs in to her account registered with the server EHR 114 by way of the second client EHR 134 executing at the second client computing device 106. The non-clinician user can be a non-clinician healthcare worker such as an administrative or clerical worker or a medical technician. In some embodiments, the non-clinician user can be a patient or other user who does not have a dedicated account registered with the server EHR 114. By way of example, the second client computing device 106 can be a kiosk computing device or mobile computing device and the client EHR 134 remains logged in to a guest user account registered with the server EHR 114. In such embodiments, the server EHR 114 updates the task data 138 to indicate that the non-clinical subtask is assigned to the guest user account. A patient can operate the second client computing device 106 while the client EHR 134 is logged in to the guest user account in order to perform a non-clinical subtask of the prescription ordering task. In some embodiments, the client EHR 134 can prompt a guest user for additional verifying information to ensure that a patient user of the guest user account is a patient to whom the non-clinical subtask pertains. In such embodiments, data pertaining to the non-clinical subtask may be displayed only when the client EHR 134 verifies additional information input by the patient user.

The second client EHR 134 causes a second EHR GUI 144 to be displayed on the display 132 of the second client computing device 106 responsive to the non-clinician user logging in to the second client EHR 134. Subsequent to the non-clinical subtask being assigned to the user account of the non-clinician user, the second client EHR 134 can cause an indicator of the non-clinical subtask to be displayed within the second EHR GUI 144. Upon selection of the indicator by the non-clinician user, the client EHR 134 displays a non-clinical subtask GUI 146 within the EHR GUI 144. The non-clinical subtask GUI 146 is configured to enable the non-clinician user to perform the non-clinical subtask of the prescription ordering task by way of the second client EHR 134.

By way of example, and not limitation, the non-clinical subtask of the prescription ordering task can include selecting a pharmacy to which to transmit a prescription order for the medication. Accordingly, the non-clinical subtask GUI 146 can include a list of pharmacies to which the prescription order can be sent by the server EHR 114. As will be described in greater detail below with respect to FIGS. 2 and 3, the non-clinical subtask GUI 146 can be configured to present various additional data that may be germane to a decision by the non-clinician user of the client EHR 134 as to which pharmacy to send the prescription order. In non-limiting examples, the non-clinical subtask GUI 146 can include a list of pharmacies with the medication currently in stock, or a price of the medication at each of a plurality of pharmacies.

Figure 2:
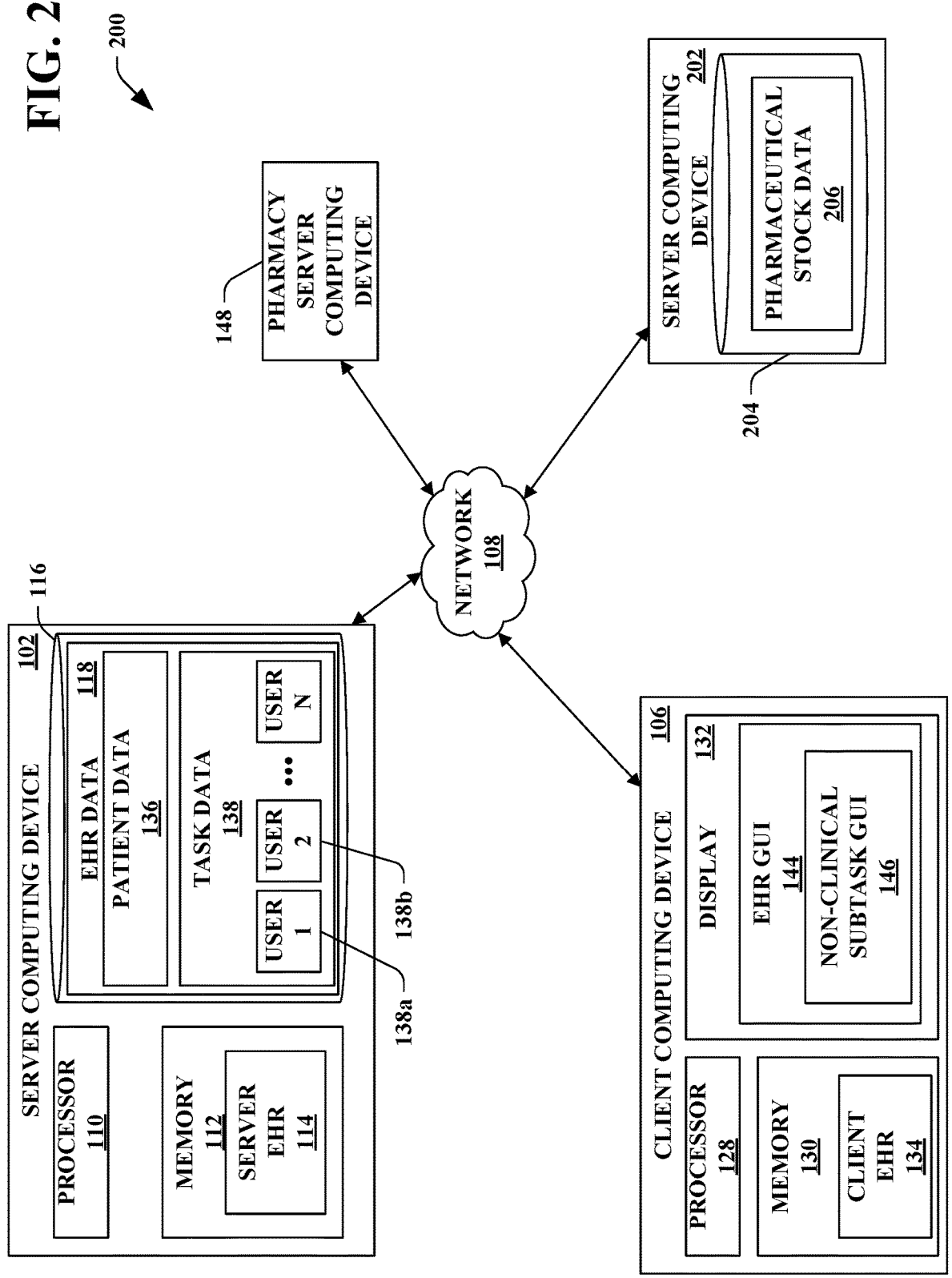
FIG. 2 is a functional block diagram of an exemplary computing system that facilitates presentment of pharmaceutical stock data in connection with performance of a prescription ordering task.

Referring now to FIG. 2, an exemplary computing system 200 is shown, wherein the non-clinical subtask GUI 146 displays data indicative of which of a plurality of pharmacies stock a selected medication. The computing system 200 includes the server computing device 102, the client computing device 106, and a second server computing device 202 that is in communication with either or both of the server computing device 102 or the client computing device 106 by way of the network 108. The server computing device 202 includes a data store 204 on which is stored pharmaceutical stock data 206. In exemplary embodiments, the server computing device 202 is a computing device operated by a pharmaceutical enterprise that is a seller or manufacturer of pharmaceuticals and other medications. The pharmaceutical stock data 206 is indicative of one or more pharmacies that currently stock a medication sold by the pharmaceutical enterprise. In a non-limiting embodiment, the server computing device 202 can receive up-to-date stock information pertaining to the medication from a plurality of computing devices each associated with a respective pharmacy (e.g., the second server computing device 148). The pharmaceutical stock data 206 can therefore comprise a list of pharmacies that currently stock a medication.

In various embodiments, either of the server EHR 114 or the client EHR 134 can be configured to query the server computing device 202 for pharmaceutical stock data relating to a medication. By way of example, and not limitation, the server EHR 114 can query the server computing device 202 for pharmaceutical stock data responsive to receipt of a prescription authorization from a client EHR in connection with performance of a clinical subtask (e.g., the client EHR 126 depicted in FIG. 1). The server EHR 114 outputs, to the server computing device 202, a medication request that comprises data indicative of a medication that is indicated in the prescription authorization. The server computing device 202 executes a search over the pharmaceutical stock data 206 to identify pharmacies that currently have the medication in stock. The server computing device 202 returns search results to the server EHR 114, the search results comprising a list of pharmacies that have the medication in stock.

In some cases, the price of a medication may vary from pharmacy to pharmacy. Accordingly, in some embodiments the pharmaceutical stock data 206 includes price data that is indicative of a price of a medication at each of a plurality of pharmacies. The computing system 200 is configured such that, when either the server EHR 114 or the client EHR 134 queries the server computing device 202 for pharmacies stocking a medication, the server computing device 202 also returns price data pertaining to the medication. Responsive to receipt of stock and price data from the server computing device 202, whether directly from the server computing device 202 or by way of the server EHR 114, the client EHR 134 displays, in the non-clinical subtask GUI 146, a list of pharmacies that stock the medication and a corresponding price of the medication at each of the listed pharmacies.

The price of a medication actually paid by a patient when purchasing the medication at a pharmacy may vary based upon the patient's insurance plan, a diagnosis of the patient, whether or not use of the medication is elective for the patient's condition, and other factors. Accordingly, the server computing device 102 can be configured to evaluate a probable final price of the medication that would be paid by a patient at each of a plurality of pharmacies listed in the non-clinical subtask GUI 146 based upon insurance data relating to the patient.

Figure 3:
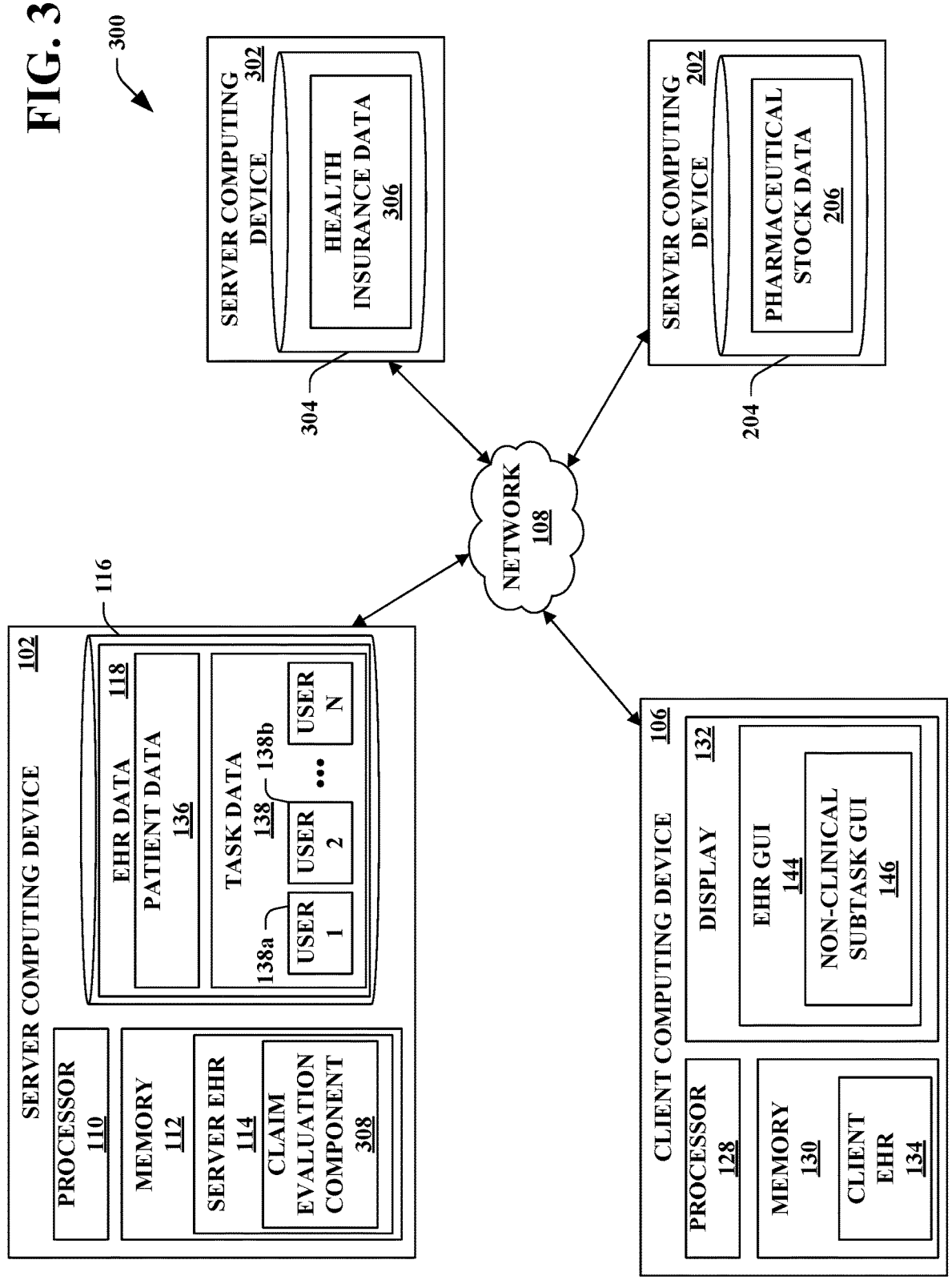
FIG. 3 is a functional block diagram of an exemplary computing system that facilitates presentment of health insurance data in connection with performance of a prescription ordering task.

By way of example, and referring now to FIG. 3, another exemplary computing system 300 that facilitates display of probable final prices of a medication in the non-clinical subtask GUI 146. The computing system 300 includes the server computing device 102 that executes the server EHR 114, the client computing device 106 that executes the client EHR 134 operated by the non-clinician user, the second server computing device 202 that stores the pharmaceutical stock data 206, and a third server computing device 302. The third server computing device 302 can be operated, maintained, or otherwise associated with a health insurance provider that provides health insurance to a patient registered with the server EHR 114. The third server computing device 302 includes a data store 304 that stores health insurance data 306. The health insurance data 306 includes data indicative of health insurance coverage with respect to a patient. By way of example, the health insurance data 306 can indicate coverage rules such as coverage limits, co-pays, out-of-pocket maximums, covered medications, covered uses of a medication, and the like. The health insurance data 306 can include data for each of a plurality of patients that are covered by the health insurance provider with which the server computing device 302 is associated. Thus, in some embodiments, the health insurance data 306 can include data that is unique to each patient covered by the health insurance provider.

Responsive to receipt of a prescription authorization from a client EHR operated by a clinician user (e.g., the client EHR 126 shown in FIG. 1), the server EHR 114 can output a query to the third server computing device 302 for insurance data relating to a patient to whom the prescription authorization pertains. By way of example, the server EHR 114 can output a query indicative of a patient, responsive to which the third server computing device 302 executes a search over the health insurance data 306 to retrieve search results that comprise insurance data pertaining to the patient. Responsive to retrieving the search results, the third server computing device 302 transmits the insurance data pertaining to the patient to the server EHR 114.

The server EHR 114 can be configured to evaluate the insurance data for the patient against the medication indicated in the prescription authorization and pricing data received from the second server computing device 202 to determine a probable final price of the medication that would be paid by the patient at a plurality of pharmacies. By way of example, the server EHR 114 can include a claim evaluation component 308. The claim evaluation component 308 receives the insurance data transmitted by the server computing device 302 and evaluates insurance coverage of the patient to determine a probable final price that would likely be paid by the patient at each of the plurality of pharmacies. In a non-limiting example, the claim evaluation component 308 can evaluate, for each of the pharmacies a portion of a price of the medication that would be covered by coverage rules indicated in the insurance data of the patient. For instance, in connection with evaluating a final price of the medication, the claim evaluation component 308 can determine whether a medication is covered by the insurance plan of the patient or whether a medication is covered for a use indicated in the prescription authorization (e.g., botulinum toxin may be covered for therapeutic uses but not cosmetic use). Further, the claim evaluation component 308 can evaluate a portion of a pharmacy price that would be paid by the patient's insurance plan based upon co-pay and co-insurance amounts indicated in the insurance data received from the third computing device 302. In some embodiments, the insurance data of the patient received from the server computing device 302 can indicate the patient's progress toward meeting a deductible or out-of-pocket maximum for the patient's insurance plan. The claim evaluation component 308 can be configured to evaluate a probable final price of the medication at a pharmacy based upon whether the purchase of the medication will cause the patient to meet her deductible and/or out-of-pocket maximum.

Responsive to determining a probable final price of the medication to the patient, the server EHR 114 transmits data indicative of the probable final price to the client EHR 134. The client EHR 134 can display, in the non-clinical subtask GUI 146, the probable final price of the medication to the patient (e.g., after insurance is accounted for) at each of the pharmacies in the list of pharmacies received from the second server computing device 202. The non-clinician user of the client EHR 134 is therefore able to determine, by reviewing the data in the non-clinical subtask GUI 146, the likely cost to the patient of the medication at each of various pharmacies that stock the medication, prior to selecting a pharmacy to which to send a prescription order for the medication.

In various embodiments, the non-clinical subtask of the prescription ordering task can include selecting a brand of the medication. For various medications, multiple brand name drugs and generic drugs may be available with identical active ingredients. For such medications, the client EHR 134 can display, in the non-clinical subtask GUI 146, a list of brands of the medication (including generics) indicated in the prescription data output to the client EHR 134 by the server EHR 114. The non-clinician user of the client EHR 134 can set forth, by way of the non-clinical subtask GUI 146, a selection of one of the brands. Responsive to receiving a selection of a brand in the displayed brands from the non-clinician user, the client EHR 134 can output prescription ordering data (as described below). In other embodiments, responsive to receiving the selection of the brand in the displayed brands, the client EHR 134 can display, in the non-clinical subtask GUI 146, a field configured to receive a selection of a pharmacy to which to send a prescription order. In such embodiments, the client EHR 134 can output the prescription ordering data to the server EHR 114 such that the prescription ordering data indicates the selected brand and the selected pharmacy.

In connection with facilitating selection of a brand of the medication, the client EHR 134 can receive information from either or both of the server computing device 202 that maintains the pharmaceutical stock data 206 or the server computing device 302 that maintains the health insurance data 306. In a non-limiting example the server EHR 114 can query the second server computing device 202 for pharmaceutical data relating to a medication, and can receive search results from the second server computing device 202 that indicate, for each of a plurality of brands (or generics) of the medication, pharmacies that stock the brand of medication and price of the brand of medication at the pharmacies. By way of further example, the search results received from the server computing device 202 can indicate that a first pharmacy stocks a first brand of the medication, whereas a second pharmacy stocks the first brand of the medication and a second brand of the medication. Continuing the example, the search results can indicate that the first brand is offered at a first price at the first pharmacy and a second price at the second pharmacy, whereas the second brand is offered at a third price at the second pharmacy. The server EHR 114 outputs the search results to the client EHR 134. Responsive to receiving the search results, the client EHR 134 causes the non-clinical subtask GUI 146 to include data indicating which brands of the medication are available at which pharmacies, and their corresponding prices at each of the pharmacies.

The server EHR 114 can further evaluate a probable final price paid for each of the brands at each of the pharmacies based upon insurance data for the patient received from the third server computing device 302. In an exemplary embodiment, the server EHR 114 receives pharmacy stock and price data from the second server computing device 202 that indicate, for each of a plurality of brands of a medication, pharmacies that stock the brand of medication and a price offered for the medication by each pharmacy. The server EHR 114 further receives insurance data pertaining to the patient from the third server computing device 302, as described in greater detail above. The claim evaluation component 308 can then evaluate, for each of the brands of the medication at each of the pharmacies, a probable final price paid by the patient based upon the insurance data that pertains to the patient. The server EHR 114 can output the pharmacy stock data and the probable final prices of the brands of the medication to the client EHR 134. The client EHR 134 then displays, in the non-clinical subtask GUI 146, the probable final prices of the brands of the medication at the various pharmacies included in the pharmacy stock data.

Responsive to completion of the non-clinical subtask of the prescription ordering task by way of the second client EHR 134, the second client EHR 134 transmits prescription ordering data to the server EHR 114. The prescription ordering data can include, for example, an indication of a pharmacy to which the prescription order is to be transmitted by the server EHR 114 or a selected brand of the medication. Responsive to receiving the prescription ordering data from the second client EHR 134, the server EHR 114 outputs a prescription order to a second server computing device 148. The second server computing device 148 can be a server computing device that is maintained, operated by, or associated with a pharmacy. In other exemplary embodiments, the second server computing device 148 can be a server computing device that is maintained, operated by, or associated with a prescription clearinghouse. In embodiments wherein the second server computing device 148 is associated with a pharmacy, the server EHR 114 outputs the prescription order to the second server computing device 148 based upon the second server computing device 148 being associated with the pharmacy indicated in the prescription ordering data received by the server EHR 114 from the client EHR 134. The prescription order includes data indicative of a medication, a patient, and the clinician's authorization to dispense the medication to the patient. In embodiments wherein the second server computing device 148 is associated with a prescription clearinghouse, the prescription order can further include data indicative of a pharmacy to which the prescription is to be sent. The second server computing device 148 can then forward the prescription order to one or more computing devices (not shown) that are associated with the pharmacy indicated in the prescription order. In some embodiments, the prescription order can include a brand of the medication selected by the non-clinician user of the client EHR 134. Accordingly, the prescription order comprises data that is generally required by a pharmacy prior to dispensing a prescribed medication to the patient.

In some instances, a patient's insurance plan requires prior authorization before authorizing payment for the medication on the patient's behalf, which generally is satisfied by supporting documentation of one or more conditions. In an example, the patient's insurance plan may require that an alternative course of treatment for an ailment is tried prior to the medication being prescribed. The claim evaluation component 308 can determine, based upon the patient's insurance data received from the third server computing device 302, whether a prior authorization for the medication is required by the patient's insurance provider. In exemplary embodiments, responsive to determining that the prior authorization is required, the server EHR 114 constructs a prior authorization response that includes documentation of a condition that is required to satisfy the prior authorization. The server EHR 114 can construct the prior authorization response based upon data pertaining to the patient that is included in the patient data 136. By way of example, the prior authorization response can indicate that the patient has received an alternate treatment prior to the medication being prescribed, wherein such alternate treatment is indicated in the patient data 136. The server EHR 114 can transmit the prior authorization response to the third server computing device 302 associated with the patient's insurance provider when the server EHR 114 transmits the prescription order to the second server computing device 148.

In other embodiments, the non-clinical subtask can include responding to a prior authorization request. In some cases, insurance data received by the server EHR 114 from the server computing device 302 does not indicate a prior authorization requirement with respect to a medication that is prescribed to the patient. In such examples, when the server EHR 114 outputs a prescription order to the second server computing device 148, the server EHR 114 may not transmit the necessary supporting documentation to the third server computing device 302 associated with the insurance provider of the patient. The third server computing device 302 can accordingly transmit a prior authorization request to the server EHR 114 prior to authorizing payment to the selected pharmacy for the medication. In other embodiments, the second server computing device 148 can transmit a prior authorization request to the server EHR 114 responsive to the second server computing device 148 receiving a prior authorization request from the third server computing device 302.

Upon receiving the prior authorization request from either of the third server computing device 302 associated with the insurance provider or the second server computing device 148, the server EHR 114 can assign, in the task data 138, a non-clinical subtask to a non-clinician one of the N users registered with the server EHR 114. The non-clinical subtask indicates that the non-clinician user is assigned to respond to the prior authorization request. Responsive to the prior authorization subtask being assigned to the non-clinician user, the client EHR 134 can present the non-clinical subtask GUI 146, such that the non-clinical subtask GUI 146 includes a field for entry of additional patient information required by the prior authorization request. The non-clinician user can then provide the additional patient information by way of the non-clinical subtask GUI 146, either by manual entry or by selection of data pertaining to the patient that is included in the patient data 136 and displayed in the non-clinical subtask GUI 146. By way of example, responsive to the non-clinician user of the client computing device 106 initiating the prior authorization subtask, the server EHR 114 can transmit patient data that may be relevant to the prior authorization request to the client EHR 134. In non-limiting examples, the patient data can include previously prescribed medications, test results, presenting symptoms, etc. The client EHR 134 can display the patient data in the non-clinical subtask GUI 146, whereupon the non-clinician user can select a portion of the patient data that is responsive to the prior authorization request. Upon receipt of a selection of the portion of the patient data, the client EHR 134 can output an indication of the portion of the patient data to the server EHR 114. The server EHR 114 can then transmit the portion of the patient data to either of the third server computing device 302 or the second server computing device 148. In an exemplary embodiment, the server EHR 114 transmits the portion of the patient data to the computing device from which the prior authorization request was received.

While certain exemplary non-clinical subtasks have been referenced herein, it is to be understood that other non-clinical subtasks of a prescription ordering task can be performed by way of the client EHR 134. In other non-limiting examples, the non-clinical subtask can include verification of various patient information by the non-clinician user of the client EHR 134, input of billing or insurance information that pertains to the patient by the non-clinician user, receipt or input of an indication of patient consent by way of the client EHR 134, etc.

With reference again briefly to FIG. 1, the client computing device 106 that displays the non-clinical subtask GUI 146 can be any of a variety of different devices that may be located at a healthcare enterprise at which a patient is receiving care. In certain non-limiting examples, the client computing device 106 can be a desktop computing device, a kiosk computing device, a mobile computing device such as a tablet. In other embodiments, a computing system can be configured such that a non-clinical subtask of a prescription ordering task can be completed by a non-clinician user (e.g., a patient) at a different location and at a later time than the clinical subtask of the prescription ordering task was completed.

Figure 4:
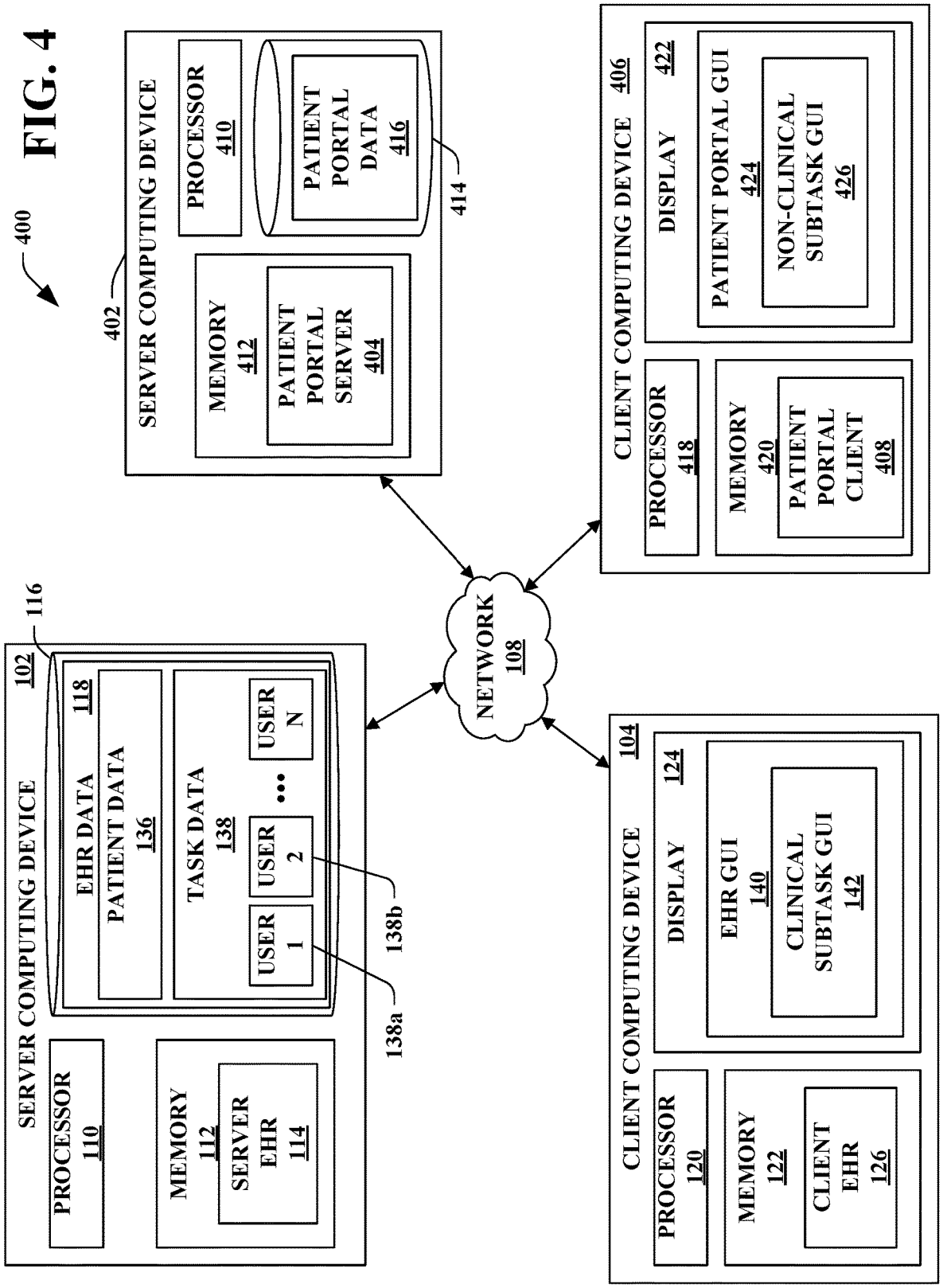
FIG. 4 is a functional block diagram of another exemplary computing system that facilitates performance of some non-clinical subtasks by a patient by way of a patient portal.

By way of example, and referring now to FIG. 4, an exemplary computing system 400 is shown that facilitates performance of a non-clinical subtask of a prescription ordering task by way of a patient portal. The computing system 400 includes the server computing device 102 that executes the server EHR 114, the client computing device 104 operated by the clinician user of the client EHR 126, a server computing device 402 that executes a patient portal server application 404, and a client computing device 406 that executes a patient portal client application 408. The server computing device 402 includes a processor 410, memory 412 that stores the patient portal server 404, and a data store 414 that stores patient portal data 416. The client computing device 406 includes a processor 418, memory 420 that stores that patient portal client 408, and a display 422 that displays a GUI 424 of the patient portal client 408.

Responsive to the clinician user of the client EHR 126 completing a clinical subtask of a prescription ordering task, the server EHR 114 can output prescription data to the patient portal server 404. The prescription data comprises an indication of a medication that is prescribed to a patient by the clinician user of the client EHR 126. The patient portal server 404, responsive to receiving the prescription data, can assign a non-clinical subtask of the prescription ordering task to a patient registered with the patient portal server 404. By way of example, the patient portal server 404 can assign the non-clinical subtask to the patient by updating the patient portal data 416 to include task data that is indicative of the non-clinical subtask). Subsequently, the patient can log in to her patient portal user account by way of the patient portal client 408 executing on the client computing device 406. The patient portal client 408 can retrieve task data assigned to the patient in the patient portal data 416 from the patient portal server 404. Responsive to retrieving the task data assigned to the patient, the patient portal client 408 displays a non-clinical subtask GUI in the patient portal GUI 424. The patient user of the patient portal client 408 can perform various of the non-clinical subtasks of the prescription ordering task referenced above. By way of example, and not limitation, the patient user can select a brand of a medication or a pharmacy to which to send a prescription order by way of the non-clinical subtask GUI 426.

Similar to embodiments discussed above with respect to FIGS. 2 and 3, pharmacies that stock the medication and probable final prices of the medication can be presented to the patient user by way of the non-clinical subtask GUI 426. In an exemplary embodiment, the server EHR 114 outputs a list of pharmacies that stock the medication and probable final prices of the medication to the patient portal server 404, which transmits these data to the patient portal client 408. In such embodiments, the server EHR 114 receives the list of pharmacies that stock the medication from the server computing device 202 associated with the pharmaceutical enterprise as discussed above with respect to FIGS. 2 and 3.

Further, the server EHR 114 computes probable final prices of the medication at a plurality of pharmacies in the manner discussed above with respect to FIGS. 2 and 3 (e.g., based upon insurance data received from the server computing device 302 associated with the insurance provider of the patient). Responsive to receiving the list of pharmacies and the probable final prices from the patient portal server 404, the patient portal client 408 displays these data in the non-clinical subtask GUI 426.

Responsive to receipt of a selection of a pharmacy to which to send the medication and/or a brand of the medication, the patient portal client 408 outputs data indicative of the selection to the patient portal server 404. Subsequently, the patient portal server 404 can output the prescription order to the server EHR 114, which then transmits the prescription order to the second server computing device 148. In other embodiments, the patient portal server 404 can output the prescription order directly to the second server computing device 148.

Figure 5:
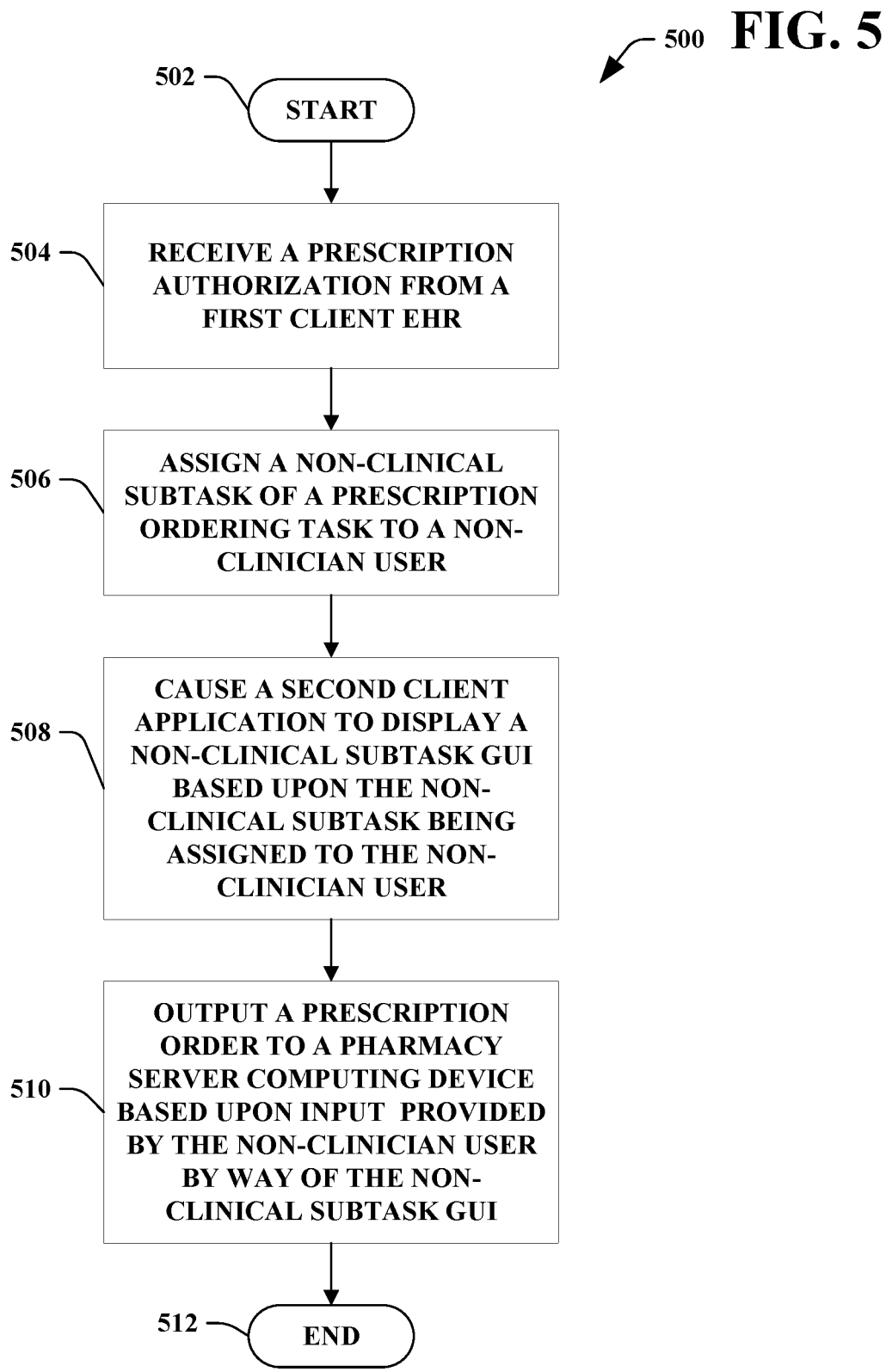
FIG. 5 is flow diagram that illustrates an exemplary methodology for performing a prescription ordering task by assignment of clinical subtasks to clinician users of a computing system and assignment of non-clinical subtasks to non-clinician users of the computing system.

FIG. 5 illustrates an exemplary methodology relating to generating prescription orders by way of an EHR, wherein a prescription ordering task is divided between a clinician user of the EHR and a non-clinician user. While the methodology is shown and described as being a series of acts that are performed in a sequence, it is to be understood and appreciated that the methodology is not limited by the order of the sequence. For example, some acts can occur in a different order than what is described herein. In addition, an act can occur concurrently with another act. Further, in some instances, not all acts may be required to implement a methodology described herein.

Moreover, the acts described herein may be computer-executable instructions that can be implemented by one or more processors and/or stored on a computer-readable medium or media. The computer-executable instructions can include a routine, a sub-routine, programs, a thread of execution, and/or the like. Still further, results of acts of the methodologies can be stored in a computer-readable medium, displayed on a display device, and/or the like.

Referring now to FIG. 5, a methodology 500, performed by an EHR server computing device, that facilitates performance of a prescription ordering task that is divided into clinical and non-clinical subtasks is illustrated. The methodology 500 begins at 502, and at 504 a prescription authorization is received from a first client EHR. The prescription authorization can be output by the first client EHR in response to a clinician user of the first client EHR completing a clinical subtask of a prescription ordering task by way of the EHR. In exemplary embodiments, the prescription authorization can indicate a medication, a patient to whom the medication is to be prescribed, and an authorization by the clinician for the medication to be dispensed to the patient.

At 506 a non-clinical subtask of the prescription ordering task is assigned to a non-clinician user registered with the EHR server. As described above with respect to FIGS. 1-4, the non-clinician user can be a healthcare worker or a patient. At 508, a second client application is caused to display a GUI for the non-clinical subtask of the prescription ordering task, based upon the non-clinical subtask being assigned to the non-clinician user. In exemplary embodiments, the second client application can be a second client EHR, a patient portal client, or the like. The non-clinical subtask GUI is configured to display information and receive input pertaining to performance of the non-clinical subtask. For example, the non-clinical subtask GUI can display a list of pharmacies from which the non-clinician user can select a pharmacy to which to send a prescription. In another example, the non-clinical subtask GUI can display price information for the medication with respect to several pharmacies, or price information for several brands of the medication.

At 510, a prescription order is output to a second server computing device, by the EHR server computing device, based upon input provided by the non-clinician user by way of the non-clinical subtask GUI. By way of example, and not limitation, the EHR server computing device can receive prescription ordering data that can indicate, inter alia, a pharmacy to which to send the prescription order, a brand of the medication to be indicated in the prescription order, additional patient information satisfying an anticipated prior authorization request, etc. The EHR server computing device can then output the prescription order to the indicated pharmacy, wherein the prescription order is for the brand of the medication indicated in the prescription ordering data. The methodology 500 completes at 512.

Figure 6:
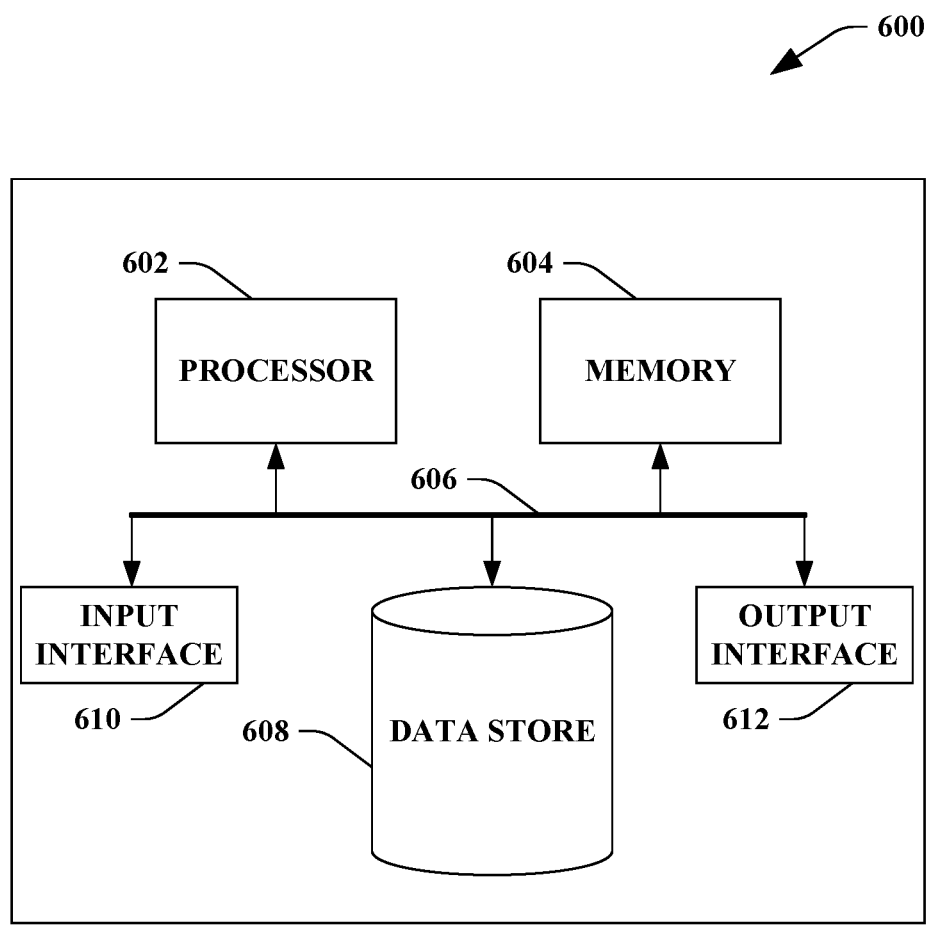
FIG. 6 is an exemplary computing system.

Referring now to FIG. 6, a high-level illustration of an exemplary computing device 600 that can be used in accordance with the systems and methodologies disclosed herein is illustrated. For instance, the computing device 600 may be used in an EHR system. By way of another example, the computing device 600 can be used in a patient portal system. The computing device 600 includes at least one processor 602 that executes instructions that are stored in a memory 604. The instructions may be, for instance, instructions for implementing functionality described as being carried out by one or more components discussed above or instructions for implementing one or more of the methods described above. The processor 602 may access the memory 604 by way of a system bus 606. In addition to storing executable instructions, the memory 604 may also store patient data, task data, insurance data, pharmaceutical stock data, etc.

The computing device 600 additionally includes a data store 608 that is accessible by the processor 602 by way of the system bus 606. The data store 608 may include executable instructions, patient data, task data, insurance data, pharmaceutical stock data, etc. The computing device 600 also includes an input interface 610 that allows external devices to communicate with the computing device 600. For instance, the input interface 610 may be used to receive instructions from an external computer device, from a user, etc. The computing device 600 also includes an output interface 612 that interfaces the computing device 600 with one or more external devices. For example, the computing device 600 may display text, images, etc. by way of the output interface 612.

It is contemplated that the external devices that communicate with the computing device 600 via the input interface 610 and the output interface 612 can be included in an environment that provides substantially any type of user interface with which a user can interact. Examples of user interface types include graphical user interfaces, natural user interfaces, and so forth. For instance, a graphical user interface may accept input from a user employing input device(s) such as a keyboard, mouse, remote control, or the like and provide output on an output device such as a display. Further, a natural user interface may enable a user to interact with the computing device 600 in a manner free from constraints imposed by input device such as keyboards, mice, remote controls, and the like. Rather, a natural user interface can rely on speech recognition, touch and stylus recognition, gesture recognition both on screen and adjacent to the screen, air gestures, head and eye tracking, voice and speech, vision, touch, gestures, machine intelligence, and so forth.

Additionally, while illustrated as a single system, it is to be understood that the computing device 600 may be a distributed system. Thus, for instance, several devices may be in communication by way of a network connection and may collectively perform tasks described as being performed by the computing device 600.

Various functions described herein can be implemented in hardware, software, or any combination thereof. If implemented in software, the functions can be stored on or transmitted over as one or more instructions or code on a computer-readable medium. Computer-readable media includes computer-readable storage media. A computer-readable storage media can be any available storage media that can be accessed by a computer. By way of example, and not limitation, such computer-readable storage media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, include compact disc (CD), laser disc, optical disc, digital versatile disc (DVD), floppy disk, and blu-ray disc (BD), where disks usually reproduce data magnetically and discs usually reproduce data optically with lasers. Further, a propagated signal is not included within the scope of computer-readable storage media. Computer-readable media also includes communication media including any medium that facilitates transfer of a computer program from one place to another. A connection, for instance, can be a communication medium. For example, if the software is transmitted from a web site, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio and microwave are included in the definition of communication medium. Combinations of the above should also be included within the scope of computer-readable media.

Alternatively, or in addition, the functionally described herein can be performed, at least in part, by one or more hardware logic components. For example, and without limitation, illustrative types of hardware logic components that can be used include Field-programmable Gate Arrays (FPGAs), Application-specific Integrated Circuits (ASICs), Application-specific Standard Products (ASSPs), System-on-a-chip systems (SOCs), Complex Programmable Logic Devices (CPLDs), etc.

What has been described above includes examples of one or more embodiments. It is, of course, not possible to describe every conceivable modification and alteration of the above devices or methodologies for purposes of describing the aforementioned aspects, but one of ordinary skill in the art can recognize that many further modifications and permutations of various aspects are possible. Accordingly, the described aspects are intended to embrace all such alterations, modifications, and variations that fall within the spirit and scope of the appended claims. Furthermore, to the extent that the term "includes" is used in either the details description or the claims, such term is intended to be inclusive in a manner similar to the term "comprising" as "comprising" is interpreted when employed as a transitional word in a claim.

What is claimed is:

1. A server computing device executing a server electronic health record application (EHR), the server computing device comprising:
 a processor; and
 memory that is operably coupled to the processor, the memory storing instructions that, when executed by the processor, cause the processor to perform acts comprising:
  receiving a prescription authorization from a first client EHR executing on a first client computing device in network communication with the server computing device, the prescription authorization being generated by the first client EHR based upon input received by way of a first GUI displayed at the first client computing device by the first client EHR, the first GUI being associated with a clinical subtask of a prescription ordering task;
  causing prescription data to be output to a second client computing device executing a second client application, the prescription data based upon the prescription authorization and indicating a medication and a clinician authorization of the medication with respect to a patient, the prescription data configured to cause the second client application to display a second GUI at the second client computing device, the second GUI associated with a non-clinical subtask of the prescription ordering task; and
  responsive to receiving prescription ordering data from the second client computing device, the prescription ordering data based upon user input received at the second client computing device by way of the second GUI, outputting a prescription order to a second server computing device, the prescription order indicative of the medication, an identity of the patient, and the clinician authorization of the medication.

2. The server computing device of claim 1, wherein the clinical subtask comprises selecting the medication to be prescribed to the patient by way of the first GUI.

3. The server computing device of claim 2, wherein the clinical subtask further comprises authorizing the medication to be dispensed to the patient, the authorizing based upon the input provided by way of the first GUI by a clinician user of the first client computing device.

4. The server computing device of claim 1, wherein the non-clinical subtask comprises selecting a pharmacy from among a plurality of pharmacies displayed in the second GUI.

5. The server computing device of claim 1, the acts further comprising:
 issuing a medication request that is indicative of the medication to a third server computing device associated with a pharmaceutical enterprise, the third server computing device storing data indicative of pharmacies that stock the medication;
 receiving results from the third server computing device responsive to the medication request, the results comprising a list of pharmacies that stock the medication; and
 causing at least a portion of the list of pharmacies to be displayed in the second GUI at the second client computing device.

6. The server computing device of claim 1, wherein the first client EHR is operated by an authorized clinician user of the first client EHR.

7. The server computing device of claim 6, wherein the second client application is operated by an authorized non-clinician user of the second client application.

8. The server computing device of claim 7, wherein the second client application is a second client EHR, wherein the authorized non-clinician user is a non-clinician healthcare worker.

9. The server computing device of claim 7, wherein the second client application is a patient portal client application, wherein the authorized non-clinician user is the patient.

10. The server computing device of claim 1, the acts further comprising:
 receiving a prior authorization request from the second server computing device, the second server computing device being associated with the pharmacy, the prior authorization request being a request for data pertaining to the patient that is not included in the prescription order;
 causing a third GUI to be displayed at the second client computing device, the third GUI comprising a prompt for second input pertaining to the prior authorization request; and
 responsive to receiving prior authorization data from the second client computing device, the prior authorization data based upon the second input, transmitting a prior authorization response to the second server computing device, the prior authorization response comprising the data pertaining to the patient that is not included in the prescription order.

11. The server computing device of claim 1, wherein the first GUI is displayed at the first client computing device based upon a clinician authorized user who is registered with the server EHR being logged into the first client EHR, wherein causing the prescription data to be output to the second client computing device comprises:
 responsive to receiving the prescription authorization from the first client EHR, assigning the non-clinical subtask of the prescription ordering task to a non-clinician user; and
 causing the prescription data to be output to the second client computing device based upon the non-clinical subtask of the prescription ordering task being assigned to the non-clinician user.

12. The server computing device of claim 11, wherein the non-clinician user is the patient, wherein assigning the non-clinical subtask of the prescription ordering task to the patient comprises outputting task data to a patient portal server application executing on a third server computing device in communication with the second client computing device, wherein the second client application is a patient portal client application configured to communicate with the patient portal server application, and wherein the patient portal server application causes the prescription data to be output to the patient portal client application.

13. A method performed by a first server computing device on which is executed a server electronic health record application (EHR), the method comprising:
 receiving a prescription authorization from a first client EHR executing on a first client computing device in network communication with the first server computing device, the prescription authorization being generated by the first client EHR based upon input received, by way of a first GUI displayed at the first client computing device by the first client EHR, from a clinician user registered with the server EHR, the first GUI being associated with a clinical subtask of a prescription ordering task;

assigning a non-clinical subtask of the prescription ordering task to a non-clinician user registered with the server EHR;

causing prescription data to be output to a second client computing device executing a second client application based upon the non-clinical subtask being assigned to the non-clinician user, the prescription data based upon the prescription authorization and indicating a medication and an authorization of the medication with respect to a patient by the clinician user, the prescription data configured to cause the second client application to display a second GUI at the second client computing device, the second GUI associated with a non-clinical subtask of the prescription ordering task; and responsive to receiving prescription ordering data from the second client computing device, the prescription ordering data based upon user input received at the second client computing device by way of the second GUI, outputting a prescription order to a second server computing device, the prescription order indicative of the medication, an identity of the patient, and the clinician authorization of the medication.

14. The method of claim 13, wherein the non-clinical subtask is assigned to the non-clinician user based upon a selection of the non-clinician user from amongst a plurality of users by the clinician user, the selection received at the first client computing device by way of the first GUI.

15. The method of claim 13, further comprising selecting the non-clinician user from amongst a plurality of users registered with the server EHR as being authorized to perform the non-clinical subtask, and wherein assigning the non-clinical subtask to the non-clinician user is based upon the non-clinician user being selected from amongst the plurality of users.

16. The method of claim 13, wherein the second computing device is included in a kiosk, wherein the second client application is configured to communicate with the server EHR.

17. The method of claim 13, wherein the second client application is a second client EHR, and wherein the first client computing device and the second client computing device are located at a same healthcare facility.

18. The method of claim 13, wherein the prescription ordering data is indicative of a pharmacy to which the prescription order is to be sent.

19. The method of claim 13, wherein the second GUI comprises a field for selection of a brand of the medication from amongst a plurality of brands of the medication, wherein the prescription ordering data includes data indicative of a brand of the medication selected by the non-clinician user, and wherein further the prescription order output to the second server computing device includes the data indicative of the brand of the medication.

20. A computer-readable medium comprising instructions that, when executed by a processor, perform the following acts:

receiving a prescription authorization from a first client electronic health record application (EHR) executing on a first client computing device in network communication with a first server computing device that executes a server EHR, the prescription authorization being generated by the first client EHR based upon input received, by way of a first GUI displayed at the first client computing device by the first client EHR, from a clinician user registered with the server EHR, the first GUI being associated with a clinical subtask of a prescription ordering task;

assigning a non-clinical subtask of the prescription ordering task to a non-clinician user registered with the server EHR;

causing prescription data to be output to a second client computing device executing a second client EHR based upon the non-clinical subtask being assigned to the non-clinician user, the prescription data based upon the prescription authorization and indicating a medication and an authorization of the medication with respect to a patient by the clinician user, the prescription data configured to cause the second client application to display a second GUI at the second client computing device, the second GUI associated with a non-clinical subtask of the prescription ordering task; and responsive to receiving prescription ordering data from the second client computing device, the prescription ordering data based upon user input received at the second client computing device by way of the second GUI, outputting a prescription order to a second server computing device, the prescription order indicative of the medication, an identity of the patient, and the clinician authorization of the medication.

* * * * *